United States Patent [19]
Collins et al.

[11] 4,322,543
[45] Mar. 30, 1982

[54] 4,5-UNSATURATED PROSTANOIC ACID DERIVATIVES

[75] Inventors: Paul W. Collins, Deerfield, Ill.; Raphael Pappo, Redwood City, Calif.

[73] Assignee: G. D. Searle & Co., Skokie, Ill.

[21] Appl. No.: 200,356

[22] Filed: Oct. 24, 1980

Related U.S. Application Data

[62] Division of Ser. No. 98,290, Nov. 28, 1979, Pat. No. 4,271,314.

[51] Int. Cl.$^3$ ............................................. C07C 177/00
[52] U.S. Cl. ...................................... 556/436; 568/379
[58] Field of Search ........................... 568/379; 556/436

[56] References Cited

U.S. PATENT DOCUMENTS

| | | | |
|---|---|---|---|
| 3,965,143 | 6/1976 | Collins et al. | 560/121 |
| 4,028,419 | 6/1977 | Nelson | 568/379 |
| 4,254,285 | 3/1981 | Wissner | 568/379 |

Primary Examiner—Robert Gerstl
Attorney, Agent, or Firm—James G. Passe

[57] ABSTRACT

4,5-Unsaturated 16-hydroxy prostanoic acid derivatives displaying valuable pharmacological properties, e.g. gastric antisecretory, are described herein.

12 Claims, No Drawings

4,322,543

4,5-UNSATURATED PROSTANOIC ACID DERIVATIVES

CROSS REFERENCE TO RELATED APPLICATION

The present case is a divisional of application Ser. No. 06/098,290, filed Nov. 28, 1979, U.S. Pat. No. 4,271,314.

SUMMARY OF THE INVENTION

The present invention is concerned with novel 4,5-unsaturated 16-hydroxy prostanoic acid derivatives represented by formula I of Chart A wherein R is —$CH_2OH$ or —$COCH_2OH$, $R_1$ is hydrogen or alkyl of 1–6 carbon atoms inclusive; n is an integer of from 2–4 inclusive; Y is a cis-vinylene or trans-vinylene group; and the (±) refers to the compound shown, its mirror image or the mixture of racemates. The present invention also relates to novel intermediate of formula XLI of Chart E which is useful in making 4,5-unsaturated prostanoic acids.

Alkyl of 1–6 carbon atoms inclusive represented in the foregoing structural formula is typified by methyl, ethyl, propyl, butyl, pentyl, hexyl and the branched chain isomers thereof.

Also included in the invention are the individual stereoisomers, and the mixture of isomers, wherein an alpha and beta isomer mixture is represented by the wavy lines in the above formula I.

Further, Alpha configurations are represented by a dashed line, and Beta configurations are represented by a thick line, in the above formula.

Compounds of the present invention wherein Y is a cis-vinylene group can be represented by formula II of Chart A wherein R, $R_1$ and n are as defined above. Preferred compounds of this group are those wherein R is —$CH_2OH$ or $COCH_2OH$. Particularly preferred compounds of this group are those compounds wherein n is 3 and $R_1$ is $CH_3$.

Compounds of the present invention wherein Y is a trans-vinylene group can be represented by formula III of Chart A wherein R, $R_1$ and n are as defined above.

DETAILED DESCRIPTION OF THE INVENTION

The novel compounds of the present invention display valuable pharmacological properties as is exemplified by their ability to inhibit the gastric secretion stimulated by secretogogues such as histamine and pentagastrin while furthermore possessing the surprising advantage of lacking the potent undesirable side-effects displayed by related substances.

The specific assay used to detect gastric anti-secretory activity is described as follows.

Adult female beagle dogs weighing 13–20 kg. are prepared with denervated fundic Heidenhain pouches. After a recovery period of at least 4 weeks following surgery, the animals are fasted for approximately 20 hours, then are placed in Pavlov stands and infused intravenously with saline solutions. The pouched secretions are collected every 15 minutes and measured for volume and total acidity by titration with 0.1 N sodium hydroxide to pH 7.0. Following a 30 minute basal secretion the dogs are infused with a saline solution of histamine dihydrochloride at a dose of 1.0 mg./hr. A steady state plateau of gastric secretion is obtained approximately 1 hour following the start of histamine infusion, at the end of which time the test compound dissolved in an ethanolic iso-osmotic phosphate buffer solution, is administered by a single intraveneous injection. The duration of the anti-secretory effects is determined and the side-effects, if any, recorded. The compound is rated active if statistically significant inhibition of secretory parameters occur following compound treatment.

Starting materials suitable for the manufacture of the compounds of the present invention are the cyclopent-1-enealkanoic acids and esters of formula IV of Chart A wherein Y is as defined hereinbefore, $R_2$ is a protecting group such as tri(lower alkyl)silyl, tetrahydrofuranyl or tetrahydropyranyl and $R_3$ is hydrogen, or alkyl of 1–6 carbon atoms, inclusive. The manufacture of these starting materials are described in Examples 1–12 and is outlined in chart B.

Introduction of the oxygenated trans-vinyl side chain at the 2-position of the cyclopentane ring is effected by reaction with a suitable organometallic reagent. The oxygenated trans-vinyl side chain groups are manufactured from the corresponding acetylenes by the process described by Pappo et al in *Chemistry, Biochemistry, and Pharmacological Activity of Prostanoids*, 17–26 (1979). Example 13 describes the manufacture of a trans-vinyl-stannane starting material from the corresponding acetylene. After the side chain is introduced, the oxygen protecting groups are conveniently removed with a weak acid solution such as acetic acid.

The compounds wherein R is a hydroxymethyl group are manufactured from the enol ether of the corresponding ester as exemplified in Example 17 and 18. Example 17 discloses a novel intermediate. The protected prostanoic ester produced by the reaction of the starting materials is treated with triethyloxonium tetrafluoroborate to produce the corresponding enol ether. The enol ether is reduced with lithium aluminum hydride and acidified with a weak acid to afford the corresponding 9-oxo-11,16-dihydroxyprost-4,13-dien-1-ol.

Compounds where R is a hydroxymethylketo group are manufactured from a corresponding hydroxycyclopentenone as exemplified in Example 11. The hydroxymethylketo compound is prepared by the conjugate addition approach.

When a resolved side chain is substituted for the racemic side chain there is formed a mixture of diastereoisomers (Examples 20 and 21). This mixture of diastereoisomers may then be chromatographed to afford the individual stereoisomeric products (Example 22).

The invention will appear more fully from the examples which follow. These examples are given by way of illustration only and are not to be construed as limiting the invention either in spirit or in scope as many modifications both in materials and in methods will be apparent from this disclosure to those skilled in the art. In these examples, temperatures are given in degrees Centigrade (C.) and quantities of materials in parts by weight unless otherwise noted.

DESCRIPTION OF THE PREFERRED EMBODIMENTS

The operation of this invention is further elaborated by the representative examples below

EXAMPLE I 4.0 Parts of 5-chloro-2-pentanone ethylene ketal is mixed with 9.0 parts of lithium bromide and 2.0 parts of diisopropylethylamine in 30 parts by volume of tetrahydrofuran which has been distilled from lithium aluminum hydride. The mixture is refluxed under nitrogen for 48 hours, cooled and poured into a mixture of ether and water for extraction. The ether layer is washed twice with water, then with 1 N hydrochloric acid and then twice again with water. The ether layer is then dried over sodium sulfate and evaporated under reduced pressure to give 5-bromo-2-pentanone ethylene ketal of formula XXI of Chart C.

EXAMPLE 2

0.1 Parts of p-toluenesulfonic acid is added to a stirred mixture of 4.2 parts 4-pentyn-1-ol and 5.0 parts dihydropyran. After about 30 minutes, the mixture is treated with 0.5 parts of triethylamine and vacuum distilled to give 2-tetrahydropyranyl-4-pentynyl ether of formula XXII of Chart C.

EXAMPLE 3

A solution containing 18.5 parts of 2-tetrahydropyranyl-4-pentynyl ether of Example 2 in 125 parts by volume of tetrahydrofuran which has been freshly distilled from lithium aluminum hydride is cooled to approximately $-30$ C and treated with 46 parts by volume of 2.4 molar n-butyl lithium solution in hexane. The solution is allowed to come to room temperature. After approximately 30 minutes at room temperature, 21 parts of 5-bromo-2-pentanone ethylene ketal of Example 1 is added, followed by the addition of 30 parts by volume of hexamethylphosphoric triamide, with stirring. After 1 hour the reaction mixture is poured into a mixture of ether and 1 N hydrochloric acid. The ether layer is washed with water, dried over sodium sulfate and stripped of solvent in vacuo to give, as a colorless, viscous liquid, the product of formula XXIII of Chart C.

EXAMPLE 4

30 Parts of the decynyl ketal of Example 3 is dissolved in a mixture of 150 parts by volume of 1 N hydrochloric acid, 200 parts by volume of tetrahydrofuran and 50 parts by volume of methanol. The solution is maintained at room temperature for 48 hours and then refluxed for 5-6 hours. The solution is then cooled to room temperature and solid potassium carbonate is added until the pH reaches 7. The solution is then stripped to ½ of its volume, diluted with water and extracted with ether twice. The ether extracts are combined, washed with water, dried over sodium sulfate and stripped of solvent to give 9-oxodec-4-yn-1-ol which is used without purification in Example 5.

EXAMPLE 5

20 Parts of 9-oxodec-4-yn-1-ol of Example 4 is dissolved in 200 parts by volume of acetone and cooled to 0 C. The cold solution is stirred and treated dropwise with 90 parts by volume of 2.67 molar Jones reagent (chromic acid and sulfuric acid and water). The acetone solution is decanted from the solid chromium salts, which are then rinsed with fresh acetone. The acetone solutions are combined and poured into a mixture of ether and water. The ether layer is separated from the water, washed once with water, and then extracted three times with 5% potassium carbonate solution. The alkaline extracts are combined, acidified with concentrated hydrochloric acid and extracted twice with ether and once with ethyl acetate. The extracts are combined, dried over sodium sulfate, and stripped of solvent to give the pure product, 9-oxodec-4-ynoic acid.

EXAMPLE 6

10 Parts of the 9-oxodec-4-ynoic acid of Example 5 is hydrogenated at room temperature in toluene containing about 0.5% quinoline with 5% palladium on barium sulfate as catalyst. The toluene solution is washed with 1 N hydrochloric acid, then water. The solution is dried over sodium sulfate and stripped of solvent to give, as a yellow oil, the product cis-9-oxodec-4-enoic acid.

EXAMPLE 7

3.2 Parts of potassium metal is added to 50 parts by volume of t-butyl alcohol and refluxed under argon. After the potassium has dissolved, a solution of 2.52 parts of cis-9-oxodec-4-enoic acid and 4.85 parts of dimethyloxalate, which has been recrystallized from hexane in 25 parts by volume of t-butyl alcohol is added dropwise to the refluxing solution over a one hour period. The reaction mixture is refluxed for 2 hours more, cooled to room temperature and filtered under argon. The orange filter cake is added to a mixture of chloroform and 1 N hydrochloric acid. The chloroform layer is washed with a saturated sodium chloride solution, dried over sodium sulfate and stripped of solvent to give the product 7-(2,3,5-trioxo-4-methoxalylcyclopentane)-hept-4-cis-enoic acid of formula XXIV of Chart C and its various tautomeric enol forms.

EXAMPLE 8

4.0 Parts of the 7-(2,3,5-trioxo-4-methoxalylcyclopentane)hept-4-cis-enoic acid of Example 7 is added to 100 parts by volume of 1 N hydrochloric acid and refluxed under argon for 3 hours. The solution is cooled to room temperature, filtered and extracted twice with ethyl acetate. The extracts were combined and washed twice with saturated sodium chloride solution, dried and stripped of solvent to give a red oil. The red oil is chromotographed on silica gel (60% ethyl acetate, 39% hexane and 1% acetic acid as eluent) to give 7-(2,3,5-trioxocyclopentane)hept-4-cis-enoic acid as a yellow solid melting at 78-80 C of formula XXV of Chart C, and its various tautomeric enol forms.

EXAMPLE 9

1.15 Parts of 7-(2,3,5-trioxocyclopentane)hept-4-cis-enoic acid is dissolved in 35 parts by volume of ethanol and 30 parts by volume of water and cooled to 0 C. 0.55 parts of sodium borohydride is dissolved in 5.0 parts by volume of water and added dropwise to the ethanol solution. After the addition is complete, the solution is stirred at 0 C for 30 minutes. The solution is poured into a solution of ethyl acetate and 1 N hydrochloric aciid. The aqueous layer is extracted three times with additional ethyl acetate. The ethyl acetate extracts are combined, washed once with saturated sodium chloride, dried over sodium sulfate and stripped of solvent to give, as a viscous yellow oil, (+)7-(2,5-dioxo-3- hydroxycyclopentane)hept-4-cis-enoic acid of formula XXVI of Chart C, and its various tautomeric enol forms.

EXAMPLE 10

2.0 Parts of (+)7-(2,5-dioxo-3-hydroxycyclopentane)hept-4-cis-enoic acid is added to 30 parts by volume of 2,2-dimethoxypropane and 4 parts by volume of 1% methanolic hydrochloride. The mixture is allowed to stand at room temperature under reduced pressure. About 4 parts by volume of ether is added and the mixture is allowed to stand at room temperature for an additional 48 hours. The solidified mixture is taken up in toluene containing 1% triethylamine, and the solution is washed successively with dilute potassium carbonate and water, dried over sodium sulfate and stripped of solvent. The residue is recrystallized from ether to give, as a white solid melting at 82–84 C, the product, (±)methyl 7-(4-hydroxy-2-methoxy-5-oxocyclopent-1-ene) hept-4-cis-enoate, of formula XXXI of Chart D.

EXAMPLE 11

100 Parts by volume of dry toluene are placed in a three-neck flask and cooled to −70 C in an isopropyl alcohol-dry ice bath. In separate dropping funnels are placed 15.5 parts by volume of 1.83 molar sodium dihydrobis-(2-methoxyethoxy)aluminate diluted with 100 parts by volume of toluene and a solution of 6.92 parts of (±)methyl 7-(4-hydroxy-2-methoxy-5-oxocyclopent-1-ene)hept-4-cis-enoate in 200 parts by volume of toluene. The two solutions are added dropwise and simultaneously to the flask. The temperature of the flask should not be allowed to exceed −60° C. during the additions. The mixture is stirred at −70° C. for 3.5 hours then at 0° C. for 15 minutes, quenched with a solution of 5.0 parts by volume methanol in 10 parts by volume of toluene, and acidified with 150 parts by volume of 1 N hydrochloric acid. The organic layer is separated, washed with water, dried over sodium sulfate and stripped of solvent. The residue is chromatographed on silica gel (70% ethyl acetate, 30% hexane as eluent) to give, as a viscous oil, (±) methyl 7-(3-hydroxy-5-oxocyclopent-1-ene)hept-4-cis-enoate of formula XXXII of Chart D.

EXAMPLE 12

2.6 Parts of (±) methyl 7-(3-hydroxy-5-oxocyclopent-1-ene)hept-4-cis-enoate is dissolved in 20 parts by volume of dimethylformamide and treated successively with 1.0 part of imidazole and 1.9 parts of triethylsilyl chloride. The solution is stirred for 1 hour at room temperature, diluted with ether, washed with water 3 to 4 times, dried over sodium sulfate and stripped of solvent. The product, which is used directly in Example 14 is (±) methyl 7-(3-triethylsilyloxy-5-oxocyclopent-1-ene)hept-4-cis-enoate of formula XXXIII of Chart D.

EXAMPLE 13

2.12 Parts of 4(RS)-trimethylsiloxy-4-methyl-1-octyne and 3.0 parts of tri-n-butyltin hydride are mixed and irradiated under argon with a sunlamp at 0° C. for 2 hours and then at 55° C. for 2 hours. The resulting product is used directly in Example 14.

EXAMPLE 14

1.0 Parts of the trans-vinylstannane product of Example 13 is dissolved in 3.0 parts by volume of dry tetrahydrofuran, cooled to −60° C. and treated with 0.87 parts by volume of a 2.3 molar solution of n-butyllithium in hexane. The solution is stirred for an hour at −60° C. and then treated with an ether solution containing 0.26 parts of copper 1-pentynylide and 0.64 parts of hexamethylphosphorous triamide. The solution is then stirred for an additional 10 minutes at −60° C. and an ether solution containing 0.35 parts of the (±) methyl 7-(3-triethylsilyloxy-5-oxocyclopent-1-ene)hept-4-cis-enoate of Example 12 is added. The solution is stirred for one hour and poured into a mixture of ether and 1 N hydrochloric acid. The ether layer was separated, washed with water twice, filtered, dried over sodium sulfate and stripped of solvent. The residue is chromatographed on silica gel (10% ethyl acetate, 90% hexane as eluent) to give the product racemic methyl 7-[3α-triethylsilyloxy-2β-(4(RS)-4-triemethylsilyloxy-4-methyl-1-trans-octenyl)-5-oxocyclo-pentane]-1α-hept-4-cis-enoate of formula XXXIV of Chart D.

EXAMPLE 15

0.30 Parts of methyl 7-[3α-triethylsilyloxy-2-β(4(RS)-4-trimethylsilyloxy-4-methyl-1-trans-octenyl)-5-oxo-cyclopentane]-1α-hept-4-cis-enoate is dissolved in 5.0 parts by volume of a 3:1:1 mixture of acetic acid:tetrahydrofuran:water and is allowed to stand at room temperature for about 30 minutes. The solution is diluted with ether, washed with water 5 times, dried over sodium sulfate and stripped of solvent. The residue is chromatographed on silica gel (100% ethyl acetate as eluent) to give, as a viscous colorless oil, the product racemic methyl 7-[3α-hydroxy-2β(4(RS)-4hydroxy 4-methyl-1-trans-octenyl)-5-oxocyclopentane]-1α-hept-4-cis-enoate of formula XXXV of Chart D.

EXAMPLE 16

1.0 Parts of racemic methyl 7-[3α-hydroxy-2β-(4(RS)-4-hydroxy-4-methyl-1-trans-octenyl)-5-oxocyclopentane]-1α-hept-4-cis-enoate is dissolved in 50 parts by volume of 95% ethanol and added to 300 parts by volume of a 7.8 pH TRIS(2-amino-2-hydroxymethyl-1,3-propanediol)buffer. This mixture is treated with 0.15 part of hog liver esterase (Sigma Chemical Co. No. E-3128) and stirred for 3 to 4 hours at room temperature. The mixture is diluted with ether, washed with 1 N hydrochloric acid, then water, dried over sodium sulfate and stripped of solvent. The residue is chromatographed on silica gel (100% ethyl acetate as eluent) to give the product racemic 7-[3α-hydroxy-2β-(4(RS)-4-hydroxy-4-methyl-1-trans-octenyl)-5-oxocyclopentane]-1α-hept-4-cis-enoic acid of formula XXXVI of Chart D.

EXAMPLE 17

1.0 Parts of the trans-vinylstannane product of Example 13 is dissolved in 3.0 parts by volume of dry tetrahydrofuran, cooled to −60° C. and treated with 0.87 parts hexane. The reaction is stirred for one hour at −60° C. and then treated with an ether solution containing 0.26 parts of copper 1-pentynilide and 0.64 parts of hexamethyl-phosphorous triamide. The solution is then stirred for an additional 10 minutes at −60° C. and an ether solution containing 0.35 parts of the (±) methyl 7-(3-triethylsilyloxy-5-oxocyclopent-1-ene)-hept-4-cis-enoate of Example 12 is added. The solution is stirred for one hour and then treated with 3.0 parts by volume of triethyloxonium tetrafluoroborate (1 molar in methylene chloride). The mixture is stirred at −50° C. for 30 minutes and then allowed to come slowly up to 0° C. The mixture is then poured into ether and dilute potassium bicarbonate solution. The layers are separated and the ether layer is washed with additional dilute potassium bicarbonate solution, dried over sodium sulfate and stripped of solvent. The residue is chromatographed on silica gel (10% ethyl acetate, 90% hexane with 0.2% triethylamine as eluent) to give racemic methyl [7-3-triethylsilyloxy-2β-(4(RS)-4-trimethyl-silyloxy-4-methyl-1-trans-octenyl)-5-ethyloxycyclopent-1(5)-ene]-1α-hept-4-cis-enoate of formula XLI of Chart E.

EXAMPLE 18

2.0 Parts of racemic methyl 7-[3-triethylsilyloxy-2-(4(RS)-4-trimethylsilyloxy-4-methyl-1-trans-octenyl)-5-ethyloxycyclopent-1(5)-ene]-1-hept-4-cis-enoate is dissolved in 100 parts by volume of dry tetrahydrofuran, cooled to 0° C. and treated with 0.3 parts of lithium aluminum hydride. After 15 minutes at 0° C., the reaction mixture is poured into ether and water. The ether layer is separated, washed again with water, dried over sodium sulfate and stripped of solvent. The residue is taken up in 50 parts by volume of 3:1:1 mixture of acetic acid, water and tetrahydrofuran and is allowed to stand at room temperature for 30 minutes. The solution is diluted with ether washed with water 4 to 5 times, dried over sodium sulfate and stripped of solvent. The residue is chromatographed on silica gel (100% ethyl acetate as eluent) to give, as a colorless viscous oil, the product racemic 7-[3α-hydroxy-2β-(4(RS)-4-hydroxy-4-methyl-1-trans-octenyl)-5-oxocyclopentane]-1α-hept-4-cis-en-1-ol of formula XLII of Chart E.

EXAMPLE 19

The $\Delta^{4,5}$ trans prostanoic acid derivatives of the present invention are prepared by the following procedures:

0.10 parts of lithium metal is added to 15 parts by volume of anhydrous ammonia in a 3-necked flask fitted with a dry ice condenser and immersed in a dry ice-isopropanol bath. 1.5 parts of the product of Example 3 and 0.5 parts by volume of t-butanol are mixed and added dropwise to the ammonia solution. The reaction mixture is stirred for 2 hours after the addition is complete. The flask is removed from the ice bath and the reaction mixture is quenched with solid ammonium chloride. Ether is then added dropwise allowing the ammonia to evaporate. The solution is poured into ether and dilute hydrochloric acid. The ether layer is separated, washed twice with dilute hydrochloric acid, then water, dried over sodium sulfate and stripped of solvent to give the product of formula XLIII of Chart E.

When the above trans compound is substituted for the acetylene compound in Example 4 and carried through Examples 5, 7, 8, 9, 10, 11, 12, 14 and 15 there is obtained the product racemic methyl 7-[3α-hydroxy-2β-(4(RS)-4-hydroxy-4-methyl-1-trans-octenyl)-5-oxocyclopentane]-1α-hept-4-trans-enoate of formula XLIV of Chart E.

When the above ester is substituted in Example 16 there is obtained the product racemic 7-[3α-hydroxy-2β-(4(RS)-4-hydroxy-4-methyl-1-trans-octenyl)-5-oxocyclopentane]-1-α-hept-4-trans-enoic acid of formula XLV of Chart E.

When the trans starting material above is substituted for the acetylene compound in Example 4 and carried through Examples 5, 7, 8, 9, 10, 11, 17 and 18 there is obtained the product racemic 7-[3α-hydroxy-2β-(4(RS)-4-hydroxy-4-methyl-1-trans-octenyl)-5-oxocyclopentane]-1-α-hept-4-trans-en-1-ol of formula XLVI of Chart E.

EXAMPLE 20

2.12 Parts of (4S)-4-trimethylsilyloxy-4-methyl-1-octyne which was obtained by the method described in "Recent Developments in the Synthesis of Antisecretory Prostaglandins", R. Pappo et al in *Chemistry, Biochemistry and Pharmacological Activity of Prostanoids*, 1979 and 3.0 parts of tri-n-butyltin hydride are mixed and irradiated under argon with a sunlamp at 0° C. for 2 hours and then at 55° C. for 2 hours. The resulting product is used directly in Example 21.

EXAMPLE 21

1.0 Parts of the trans-vinylstannane product of Example 20 is dissolved in 3.0 parts by volume of dry tetrahydrofuran, cooled to −60° C. and treated with 0.87 part by volume of a 2.3 molar solution of n-butyllithium in hexane. The solution is stirred for an hour at −60° C. and then treated with an ether solution containing 0.26 parts of copper 1-pentynylide and 0.64 part of hexamethylphosphorous triamide. The solution is then stirred for an additional 10 minutes at −60° C. and an ether solution containing 0.35 parts of the racemic methyl 7-(3-triethylsilyloxy-5-oxocyclopent-1-ene)hept-4-cis-enoate of Example 12 is added. The solution is stirred and poured into a mixture of ether and 1 N hydrochloric acid. The ether layer was separated, washed with water twice, filtered, dried over sodium sulfate and stripped of solvent. The residue is chromatographed on silica gel (10% ethyl acetate, 90% hexane as eluent) to give a mixture of diastereoisomers methyl 7-[3(S)-triethylsilyloxy-2α-(4(S)-trimethylsilyloxy-4-methyl-1-trans-octenyl-5-oxocyclopentane]-1β-hept-4-cis-enoate of formula LI of Chart F and methyl 7-[3(R)-triethylsilyloxy-2β-(4(S)-trimethylsilyloxy-4-methyl-1-trans-octenyl)-5-oxocyclopentane]1α-hept-4-cis-enoate of formula LII of Chart F.

EXAMPLE 22

0.30 Parts of the diastereoisomers of Example 21 is dissolved in 5.0 parts by volume of a 3:1:1 mixture of acetic acid:tetrahydrofuran:water and is allowed to stand at room temperature for about 30 minutes. The solution is diluted with ether, washed with water 5 times, dried over sodium sulfate and stripped of solvent. The residue is chromatographed on hydroxyapatite (6% n-butanol, 94% cyclohexane as eluent) to give the products methyl 7-[3(S)-hydroxy-2α-(4(S)-hydroxy-4-methyl-1-trans-octenyl)-5-oxocyclopentane]-1β-hept-4-cis-enoate and methyl [7-3(R)-hydroxy-2β-(4(S)-hydroxy-4-methyl-1-trans-octenyl)-5-oxocyclopentane]-1α-hept-4-cis-enoate.

EXAMPLE 23

0.365 Parts of racemic 7-[3(α)-hydroxy-2β-(4-(RS)-4-hydroxy-4-methyl-1-trans-octenyl)-5-oxocyclopentane]-1α-hept-4-cis-enoic acid of Example 16 is dissolved in 5.0 parts by volume of dimethylsulfoxide and treated with 1.0 parts isopropyl iodide and 0.35 parts of N,N-diisopropylethylamine. The solution is stirred overnight. The solution is diluted with ether, washed with cold dilute hydrochloric acid and then 2-3 times with water, dried and chromatographed on silica gel (100% ethyl acetate as eluent) to give the product racemic isopropyl 7-[3(α)-hydroxy-2β-(4(RS)-4-hydroxy-4-methyl-1-trans-octenyl)-5-oxocyclopentane]-1α-hept-4-cis-enoate of formula LIII of Chart F.

EXAMPLE 24

The hydroxycyclopentenone of Example 11 (500 mg) is dissolved in 7 ml of acetone and treated with 7 ml of one N hydrochloric acid. The mixture is allowed to stand at room temperature for 48 hours. The solution is stripped under reduced pressure to remove most of the acetone. The aqueous solution is extracted several times with ethyl acetate. The extracts are combined washed once with saturated sodium chloride solution and dried over sodium sulfate and then stripped again to yield an oil, cyclopentenoic acid.

A solution of the cyclopentenoic acid (500 mg) imidazole (600 mg) in 8 to 10 ml of dimethylformamide (DMF) is treated at room temperature with stirring with 800 mg of t-butyl dimethyl silyl chloride. After one hour, the reaction mixture is poured into a one to one mixture of hexane/ether and water. The organic layer is washed with water three times, dried over sodium sulfate, and stripped again to yield an oil. Chromatography using a 10% ethyl acetate 90% hexane solvent system on silica gel gives 600 mg of pure product, a bis silyl ether. 600 mg of this silyl ether is dissolved in about five ml of methylene chloride and then cooled to 0° C. in an ice bath. It is then treated with two to three drops of (DMF) and then with oxalyl chloride (200 mg) in one ml of methylene chloride. The reaction mixture is allowed to come to room temperature. After one hour the solution is blown to dryness. The residue is then dissolved in 6 ml of chlorobenzene and treated with 700 mg of tris (trimethyl-silyloxy-ethylene) prepared as described by A. Wissner *J. Org. Chem.*, 44, 4617 (1979) and refluxed under argon for 3 to 4 hours. The mixture is then cooled and stripped under reduced pressure to a paste which is dissolved in tetrahydrofuran (3–4 ml) treated with one ml of one N hydrochloric acid and then refluxed under argon for one hour. The solution is cooled, diluted with ethyl acetate, and washed with saturated sodium chloride solution. The aqueous wash is extracted with chloroform twice. All extracts are then combined and dried over sodium sulfate, then stripped. Chromatography of the residue on silica gel using 80% ethyl acetate 20% hexane solvent system gives an oil. The oil (cyclopentane product) (110 mg) is dissolved in 2 ml of (DMF) containing 150 mg of imidazole and then is treated with stirring with 150 mg of triethyl silyl chloride. The reaction mixture is stirred at room temperature for one hour, and is diluted with ether, washed with water three times, and then dried over sodium sulfate and stripped to give the bis silyl ether a compound according to Formula LIV of Chart F.

EXAMPLE 25

The bis silyl ether of Example 24 is used in the process described in Example 15 to yield Racemic 4α-hydroxy-3β-(4S)-(4-hydroxy-4-methyl-1E-octenyl)-2α-(8-hydroxy-7-oxo-3Z-octenyl)cyclopentanone a compound according to Formula LV of Chart F.

EXAMPLE 26

The product of Example 20 is substituted in the process described in Example 17. The product from this is then substituted in the process described in Example 18. The isomers are then separated according to the process in Example 22 to yield 7-[3S-hydroxy-2α-((4S)-4-hydroxy-4-methyl-1-trans-octenyl)-5-oxocyclopentane]-1β-hept-4-cis-en-1-ol, compound LXI of Chart G and 7-[3R-hydroxy-2β-(4S)-4-hydroxy-4-methyl-1-trans-octenyl)-5-oxocyclopentane]-1αhept-4-cis-en-1-ol, compound LXII of Chart G.

EXAMPLE 27

The bis silyl ether of Example 24 is substituted in the process described in Example 21, the product of this reaction is substituted in the process described in Example 22 to yield 4R-hydroxy-3β-(4S-4-hydroxy-4-methyl-1E-octenyl)-2α-(8-hydroxy-7-oxo-3Z-octenyl)cyclopentanone compound LXIII of Chart G and 4S-hydroxy-3α-(4S-4-hydroxy-4-methyl-1E-octenyl)-2β-(8-hydroxy-7-oxo-3Z-octenyl)cyclopentanone compound LXIV or chart G.

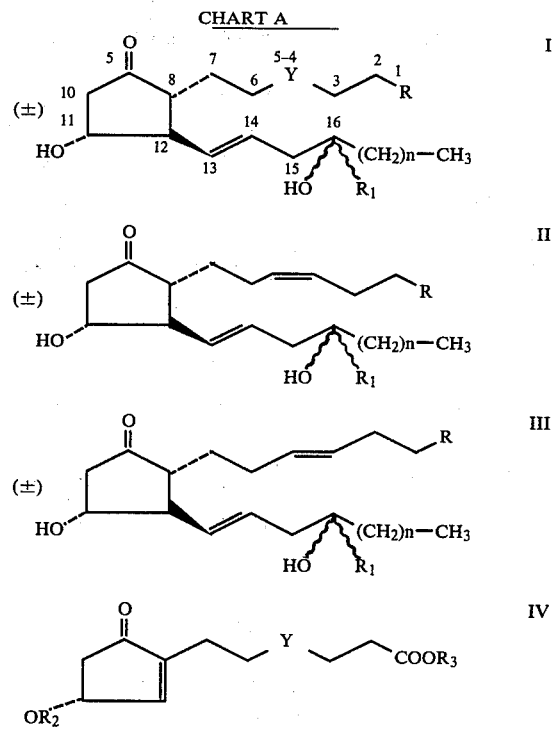

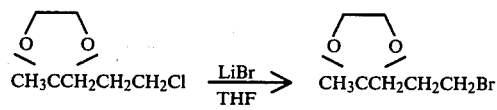

+

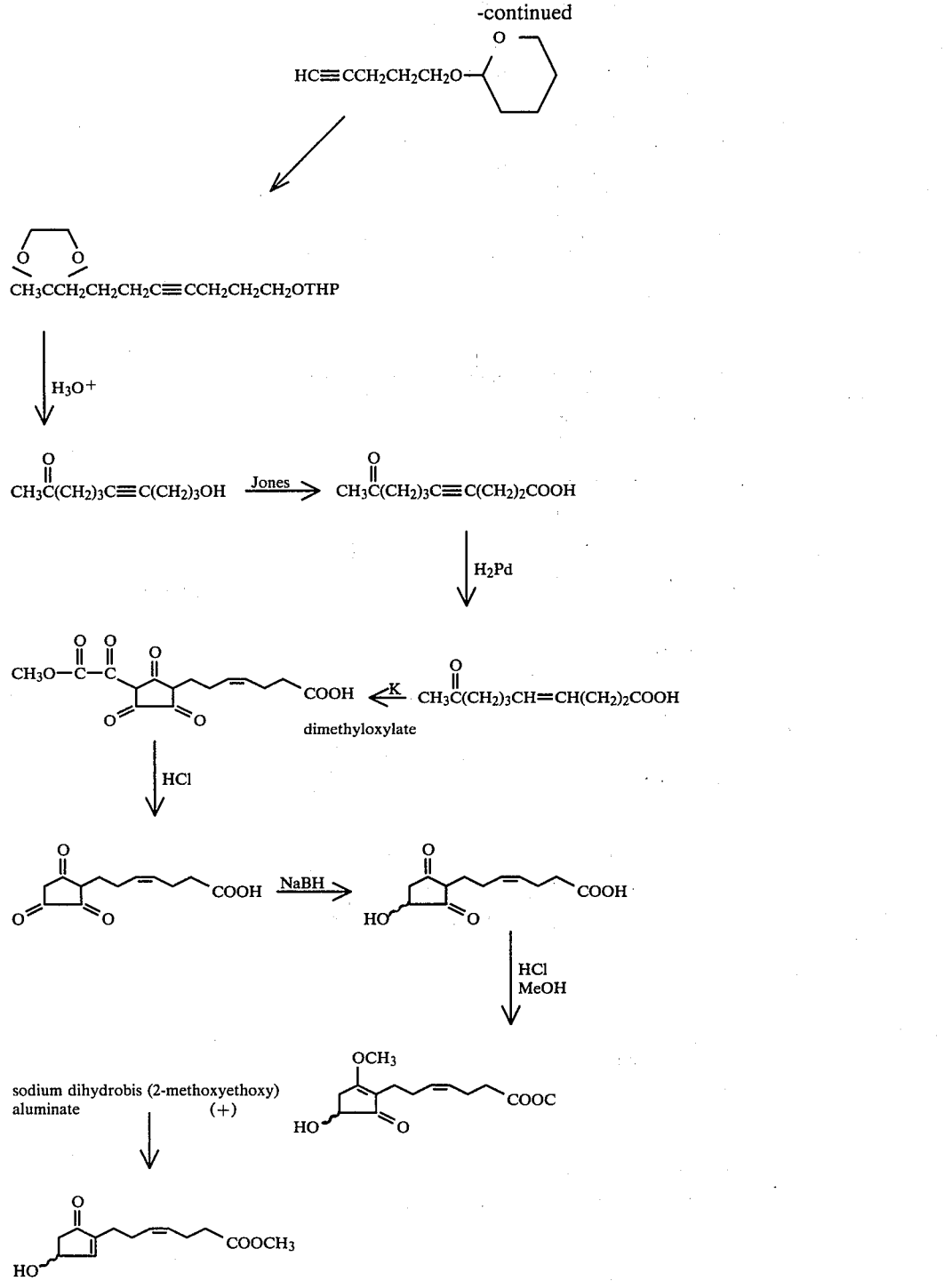
CHART C
CH₃CCH₂CH₂CH₂Br
HC≡CCH₂CH₂CH₂O—[THP]
XXI
XXII
CH₃CCH₂CH₂CH₂C≡CCH₂CH₂CH₂O—[THP]
-continued
XXIII
HC≡CCH₂CH₂CH₂O—[THP]

13 -continued
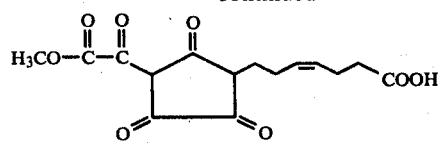 XXIV
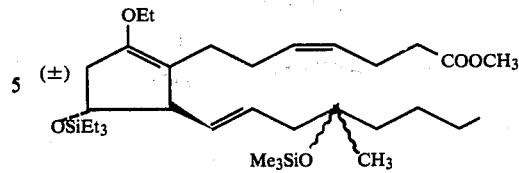 XXV
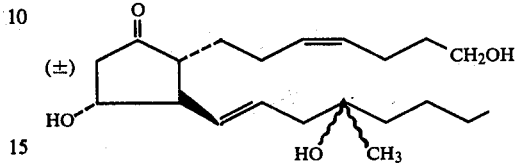 XXVI
CHART D
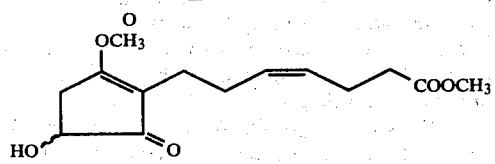 XXXI
XXXII
XXXIII
XXXIV (±)
XXXV (±)
XXXVI (±)
CHART E
14 -continued
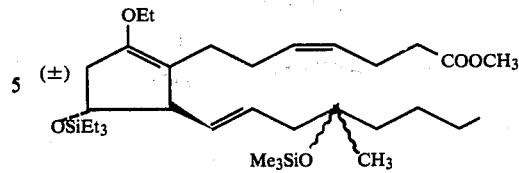 XLI (±)
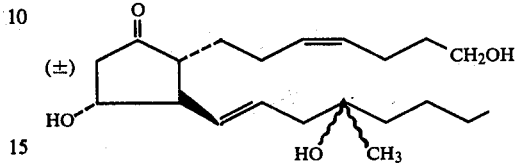 XLII (±)
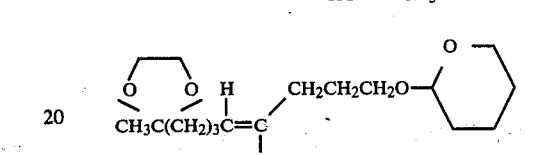 XLIII
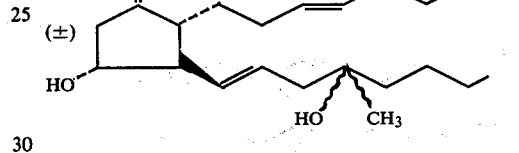 XLIV (±)
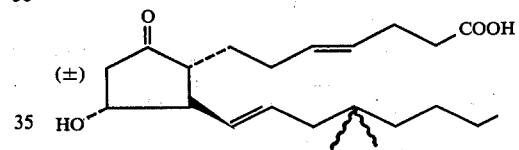 XLV (±)
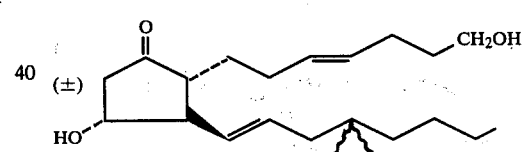 XLVI (±)
CHART F
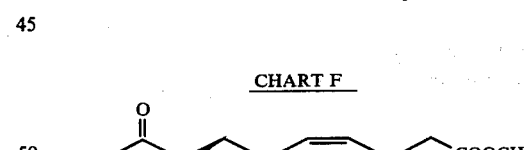 LI
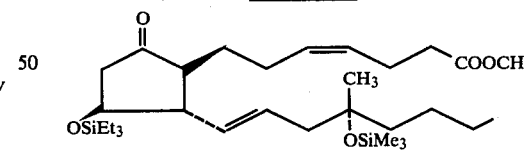 LII
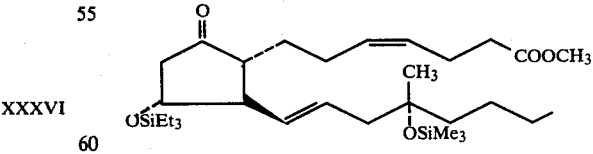 LIII (±)

CHART G

What is claimed is:

1. A compound of the formula:

wherein R is —COCH₂OH or —CH₂OH;
wherein $R_1$ is:
(a) hydrogen; or
(b) alkyl of 1 to 6 carbon atoms inclusive;
wherein n is an integer from 2 through 4 inclusive;
wherein Y is a cis-vinylene or trans-vinylene group; and
wherein the (+) refers to the structure of formula I, its mirror image or the mixture of racemates.

2. A compound according to claim 1 wherein R is —CH₂OH.

3. A compound according to claim 2 wherein $R_1$ is methyl.

4. Racemic 7-[3α-hydroxy-2β-(4(RS)-hydroxy-4-methyl-1-octenyl)-5-oxocyclopentane]-1α-hept-4-cis-en-1-ol, a compound according to claim 3.

5. 7-[3S-hydroxy-2α-((4S)-4-hydroxy-4-methyl-1-trans-octenyl)-5-oxocyclopentane]-1β-hept-4-cis-en-1-ol a compound according to claim 3.

6. 7-[3R-hydroxy-2β-((4S)-4-hydroxy-4-methyl-1-trans-octenyl)-5-oxocyclopentane]-1α-hept-4-cis-en-1-ol, a compound according to claim 3.

7. A compound according to claim 1 wherein R is —COCH₂OH.

8. A compound according to claim 7 wherein $R_1$ is methyl.

9. Racemic 4α-hydroxy-3β-(4(RS)-4-hydroxy-4-methyl-1E-octenyl)-2α-(8-hydroxy-7-oxo-3A-octenyl) cyclopentanone a compound according to claim 8.

10. 4R-hydroxy-3β-(4S-4-hydroxy-4-methyl-1E-octenyl)-2α-(8-hydroxy-7-oxo-3Z-octenyl) cyclopentanone a compound according to claim 8.

11. 4S-hydroxy-3α-(4S-4-hydroxy-4-methyl-1E-octenyl)-2β-(8-hydroxy-7-oxo-3Z-octenyl) cyclopentanone a compound according to claim 8.

12. Racemic methyl 7-[3-triethylsilyloxy-2β-(4(RS)-4-trimethylsilyloxy-4-methyl-1-trans-octenyl)-5-ethyloxycyclopent-1(5)-ene]-1α-hept-4-cis enoate.

* * * * *